(12) United States Patent
Jung et al.

(10) Patent No.: US 8,067,341 B2
(45) Date of Patent: Nov. 29, 2011

(54) METHOD FOR FABRICATING A BIOCHIP USING THE HIGH DENSITY CARBON NANOTUBE FILM OR PATTERN

(76) Inventors: Hee Tae Jung, Daejeon (KR); Sang Yup Lee, Daejeon (KR); Dae Hwan Jung, Daejeon (KR); Byung Hun Kim, Seoul (KR); Young Koan Ko, Daejeon (KR)

(*) Notice: Subject to any disclaimer, the term of this patent is extended or adjusted under 35 U.S.C. 154(b) by 580 days.

(21) Appl. No.: 10/805,044

(22) Filed: Mar. 19, 2004

(65) Prior Publication Data

US 2005/0019791 A1  Jan. 27, 2005

(30) Foreign Application Priority Data

Jul. 24, 2003  (KR) .................. 10-2003-0051140
Jul. 26, 2003  (KR) .................. 10-2003-0051826

(51) Int. Cl.
*C40B 60/00* (2006.01)
(52) U.S. Cl. ............... 506/33; 435/4; 435/6; 435/7.1; 977/742
(58) Field of Classification Search ................. None
See application file for complete search history.

(56) References Cited

U.S. PATENT DOCUMENTS

| 5,474,895 | A | 12/1995 | Ishii et al. |
| 5,866,434 | A | 2/1999 | Massey et al. |
| 6,872,681 | B2 * | 3/2005 | Niu et al. ................. 502/101 |
| 7,272,511 | B2 * | 9/2007 | Occhipinti et al. ........... 702/32 |
| 2002/0172963 | A1 | 11/2002 | Kelley et al. |
| 2002/0179434 | A1 | 12/2002 | Dai et al. |
| 2003/0012723 | A1 | 1/2003 | Clarke |
| 2004/0028901 | A1 * | 2/2004 | Rumpf et al. ............... 428/375 |
| 2004/0142285 | A1 | 7/2004 | Jung et al. |
| 2005/0214195 | A1 | 9/2005 | Jung et al. |
| 2006/0003401 | A1 | 1/2006 | Lee et al. |

FOREIGN PATENT DOCUMENTS

| KR | 20040107225 A | 12/2004 |
| KR | 20040107763 A | 12/2004 |
| WO | 9607487 A1 | 3/1996 |
| WO | 02086168 A1 | 10/2002 |
| WO | WO 03/016901 A1 | 2/2003 |

OTHER PUBLICATIONS

Mamedove et al 2002 Nature Materials 1:190-194.*
Chiu et al (2002 Applied Physics Letters 80:3811-3813).*
Dal, H., *Acc. Chem. Res.*, 36:1035-1044, 2002.
Nan, X. et al., *J. Colloid Interface Sci.*, 245:311-8, 2002.
Rouse, J.H. et al., *Nano Lett.*, 3:59-62, 2003.
Sottropoulou, S. et al., *Anal. Bioanal. Chem.*, 375:103-5, 2003.
Erlanger, B.F. et al., *Nano Lett.*, 1:465-7, 2001.
Azamian, B.R. et al., *JACS*, 124:12664-5, 2002.
Star, A. et al., *Nano Lett.*, 3:459-63, 2003.
Rogers, Y. et al., *Anal. Biochem.*, 266:23-30, 1999.
Hu, J. et al., *Nuc. Acid. Res.*, 29:106-10, 2001.
Taton, T.A. et al., *Science*, 289:1757-60, 2000.
Alexandre, I. et al., *Anal. Biochem.*, 295:1-8, 2001.
Cal, H. et al., *Analyst.*, 127:803-8, 2002.
Cal. H. et al., *Anal. Bioanal. Chem.*, 375:287-93, 2003.
Chen, R.J. et al., *Proc. Natl. Acad. Sci. USA*, 100:4984-9, 2003.
Toriba, A. et al., *Biomed. Chromatogr.*, 17:128-32, 2003.
Syrzycka, M. et al., *Anal. Chim. Acta*, 484:1-14, 2003.
Grow, A.E. et al., *J. Microbio. Meth.*, 53:221-33, 2003.
Williams, K.A. et al., *Nature*, 420:761, 2001.
Li, J. et al., *Nano Lett.*, 3:597-602, 2003.
Kouwenhoven, L., *Science*, 275:1896-97, 1997.
Bandyopadhyaya, R. et al., "Stabilization of Individual Carbon Nanotubes in Aqueous Solutions", Nov. 22, 2001, pp. 25-28, vol. 2, No. 1.
Bockwrath, M. et al, "Single Electron Transport in Ropes of Carbon Nanotubes", "Science", Mar. 28, 1997, pp. 1922-1925, vol. 275.
Chambers, G. et al., "Characterization of the Interaction of Gamma Cyclodextrin with Single Walled Carbon Nanotubes", "Nano Letters", Apr. 19, 2003, pp. 843-846, vol. 3, No. 6, Publisher: American Chemical Society.
Chen, J. et al. , "Solution Properties of Single Walled Carbon Nanotubes", "Science", Oct. 2, 1998, pp. 95-98, vol. 282.
Chen, J. et al., "Lifetime- and Color-Tailored Fluorophores in the Micro- to Millisecond Time Regime", "J. Am. Chem. Soc.", Jan. 15, 2000, pp. 657-660, vol. 122, Publisher: American Chemical Society.
Chen, J. et al., "Noncovalent Engineering of Carbon Nanotube Surfaces by Rigid Functional Conjugated Polymers", "J. Am. Chem. Society Communications", Jul. 13, 2002, pp. 9034-9035, vol. 124.
Dahne, L. et al., "Fabrication of Micro Reaction Cages with Tailored Properties", "J. Am. Chem. Soc.", May 18, 2001, pp. 5431-5436, vol. 123, Publisher: American Chemical Society.
Georgakilas, V. et al., "Amino Acid functionalisation of water soluble carbon nanotubes", "Chem. Commun.", Nov. 14, 2002, pp. 3050-3051.
Hergenrother, P. et al., "mall-Molecule Microarrays: Covalent Attachment and Screening of Alcohol-Containing Small Molecules on Glass Slides", "J. Am. Chem. Soc.", 2000, pp. 7849-7850, vol. 122, Publisher: American Chemical Society.
Houseman, B. et al., "Towards quantitative assays with peptide chips: a surface engineering approach", "Trends in Biotechnology", May 10, 2002, pp. 279-281, vol. 20, No. 7, Publisher: Elsevier Science Ltd.

(Continued)

*Primary Examiner* — Christopher M Gross
(74) *Attorney, Agent, or Firm* — Steven J. Hultquist; Kelly K. Reynolds; Hultquist IP (57) ABSTRACT

Carbon nanotube (CNT) films, patterns and biochips and methods of making the same are provided. Such a biochip comprises a bio-receptor attached by means of an exposed chemical functional group on a surface of a high density CNT film or pattern produced by repeated lamination of CNTs on a substrate with exposed amine groups. Various types of CNT-biochips may be fabricated by bonding of bio-receptors to a CNT pattern (or film) containing exposed carboxyl groups or modified by various chemical functional groups. Further, the CNT-biochip may be used to measure an electrical or electrochemical signal using both conductor and semiconductor properties of the CNT, thereby not needing labeling. Upon fluorescent measurement of DNA hybridization using such a CNT-DNA chip it is possible to show more distinct signals useful for genotyping, mutation detection, pathogen identification and the like.

28 Claims, 8 Drawing Sheets

OTHER PUBLICATIONS

Jiang, K. et al., "Selective Attachment of Gold Nanoparticles to Nitrogen-Doped Carbon Nanotubes", "Nano Letters", Feb. 13, 2003, pp. 275-277, vol. 3, No. 3, Publisher: American Chemical Society.

Kang, Y. et al., "Micelle encapsulated Carbon Nanotubes: A Route to Nanotube Composites", "J. Am. Chemical Society", Apr. 19, 2003, pp. 5650-5651, vol. 125.

Matsushige, K. et al., "Nanoscale control and detection of electric dipoles in organic molecules", "Nanotechnology 9", 1998, pp. 208-211, Publisher: IOP Publishing Ltd.

Mitchell, C. et al., "Dispersion of Functionalized Carbon Nanotubes in Polystyrene", "Macromolecules", Sep. 28, 2002, pp. 8825-8830, vol. 35, Publisher: American Chemical Society.

Moll, D. et al., "S-layer streptavidin fusion proteins as template for nanopatterned molecular arrays", "PNAS", Nov. 12, 2002, pp. 14646-14651, vol. 99, No. 23.

Oconnell, M. et al., "Reversible water solubilization of single walled carbon nanotubes by polymer wrapping", "Chemical Physical Letters", Jul. 31, 2001, pp. 265-271, vol. 342, Publisher: Elsevier.

Pantarotto, D. et al., "Immunization with Peptide-Functionalized Carbon Nanotubes Enhances Virus Specific Neutralizing Antibody Responses", "Chemistry and Biology", Oct. 2003, pp. 961-966, vol. 10.

Pum, D. et al., "The application of bacterial S-layers in molecular nanotechnology", "Nanotechnology", Jan. 1999, p. 8-, vol. 17.

Rao, A. et al., "Diameter Selective Raman Scattering from Vibrational Modes in Carbon Nanotubes", "Science", Jan. 10, 1997, pp. 187-191, vol. 275.

Schena, Mark, et al., "Quantitative monitoring of gene expression patterns with a complementary DNA microarray", "Science", Oct. 20, 1995, pp. 467-470, vol. 270.

Star, A. et al., "Dipsersion and Solubilization of Single Walled Carbon Nanotubes with a Hyperbranched Polymer", "Macromolecules", Aug. 8, 2002, pp. 7516-7520, vol. 35.

Stelzle, M., et al., "On the Application of Supported Bilayers as Receptive Layers for Biosensors with Electrical Detection", "J. Phys. Chem.", 1993, pp. 2974-2981, vol. 97, Publisher: American Chemical Society.

Vijayendran, Ravi A., et al., "A Quantitative Assessment of Heterogeneity for Surface-Immobilized Proteins", "Analytical Chemistry", Feb. 1, 2001, pp. 471-480, vol. 73, No. 3, Publisher: American Chemical Society.

Wang, Z. et al., "A selective voltammetric method for uric acid detection at B-cyclodextrin modified electrode incorporating carbon . . . ", "The Royal Society of Chemistry", Aug. 29, 2002, pp. 1353-1358, vol. 127.

Copending U.S. Appl. No. 10/860,544, filed Jun. 3, 2004.

* cited by examiner

METHOD FOR FABRICATING A BIOCHIP USING THE HIGH DENSITY CARBON NANOTUBE FILM OR PATTERN

BACKGROUND OF THE INVENTION

1. Field of the Invention

The present invention relates to a biochip comprising a bio-receptor chemically or physicochemically attached to a high density carbon nanotube (CNT) film or pattern having chemical functional groups exposed, in which the bio-receptor is capable of binding to a target biomaterial, and a method for preparing the same.

2. Background of the Related Art

Carbon nanotube (CNT) is an allotrope of carbon, which consists of carbons exists abundantly on the earth. They are tubular materials where a carbon atom is connected to other carbons in the form of a hexagonal honeycomb structure. Their diameter is about size of nanometer ($1/10^9$ meter). CNT is known to have excellent mechanical properties, electrical selectivity, field emission properties and highly efficient hydrogen storage properties and be new and almost defect-free of all the existing materials.

Because of their properties of excellent structural rigidity, chemical stability, ability to act as ideal one-dimensional (1D) "quantum wires" with either semiconducting or metallic behaviors and a large aspect ratio, CNT exhibits a broad range of potential applications as a basic material of flat panel displays, transistors, energy reservoirs, etc., and as various sensors with nanosize (Dai, H., *Acc. Chem. Res.*, 35:1035-1044, 2002).

In order to apply such properties more diversely, the purified single-walled CNT has been cut into short nanotube pieces using an acid. The cut CNT pieces have mainly —COOH chemical functional groups at a part of ends and sidewall of the open tube. The properties of the CNT have been modified by chemical binding of various materials using these chemical functional groups. Further, there have been reported that the functional group of CNT was substituted for —SH group by chemical manipulation and patterned on a gold surface (Nan, X. et al., *J. Colloid Interface Sci.*, 245:311-8, 2002) and that CNT was immobilized on substrate using the electrostatic method (Rouse, J. H. et al., *Nano Lett.*, 3:59-62, 2003). However, the former has disadvantages of the low CNT surface density and the weak bonding, and the latter also has a fatal disadvantage that the patterning method for selective immobilization on the surface cannot be applied. Therefore, there is an urgent demand for developing a new type surface immobilizing method with high density.

Recently, researches are being conducted to detect reactions both protein-protein and protein-ligand by means of electrochemical changes of CNT after immobilization of a biomaterial (Dai, H. et al., *ACC. Chem. Res.*, 35:1035-44, 2002; Sotiropoulou, S. et al., *Anal. Bioanal. Chem.*, 375:103-5, 2003; Erlanger, B. F. et al., *Nano Lett.*, 1:465-7, 2001; Azamian, B. R. et al., *JACS*, 124:12664-5, 2002). A representative example of a protein-ligand reaction is an avidin-biotin reaction. Star et al. formed a channel on a substrate, which had been treated with a polymer, using CNT and measured the binding activity of streptoavidin by means of an electrochemical method (Star, A. et al., *Nano Lett.*, 3:459-63, 2003).

The reasons that CNT attracts public attention as a biochip are as followings: Firstly, it needs no labeling; secondly, it has high sensitivity to signal change; and thirdly, it is capable of reacting in an aqueous solution without deterioration of a protein. The combination of a new nanomaterial and a biological system will create important fusion technologies in respective fields of disease diagnosis (hereditary diseases), proteomics and nanobiotechnology.

In order to develop a rapider and cheaper biochip, many researches have been conducted on technologies of DNA hybridization detection. Various labeling technologies for detecting DNA hybridization have been developed. An effective surface treatment capable of increasing hybridization efficiency and simultaneously, removing the background from non-specific binding is required to detect the DNA hybridization effectively using the DNA chip. Many researches have been conducted to prepare a surface-treated DNA chip platform (Rogers, Y. et al., *Anal. Biochem.*, 266:23-30, 1999; Hu, J. et al., *Nuc. Acid. Res.*, 29:106-10, 2001). Also, various methods for detecting DNA hybridization were developed, which include the scanometric method, the calorimetric method, a method using nanoparticle, a method using electrochemistry, and etc. (Taton, T. A. et al., *Science*, 289:1757-60, 2000; Alexandre, I. et al., *Anal. Biochem.*, 295:1-8, 2001; Cai, H. et al., *Analyst.*, 127:803-8, 2002; Cai, H. et al., *Anal. Bioanal. Chem.*, 375:287-93, 2003).

Besides many applications with CNT in the bioengineering field have been recently being appeared. It is being suggested that the applicability of CNT to biochips, such as glucose biosensors, detecting protein, detecting a certain DNA sequence and the like (Sotiropoulou, S. et al., *Anal. Bioanal. Chem.*, 375:103-5, 2003; Chen, R. J. et al., *Proc. Natl. Acad. Sci.* USA, 100:4984-9, 2003; Cai, H. et al., *Anal. Bioanal. Chem.*, 375:287-93, 2003). Screening bio-molecules from multilayer based on CNT can increase the amount of immobilized bio-substances, such as DNAs and detecting sensitivity to the bio-substances, since the CNT has wide surface area and high electric conductivity.

At the present time, the most universal method for detecting the result of the reaction in a biochip is to use conventional fluorescent materials and isotopes (Toriba, A. et al., *Biomed. Chromatogr.*, 17:126-32, 2003; Syrzycka, M. et al., *Anal. Chim. Acta*, 484:1-14, 2003; Grow, A. E. et al., *J. Microbio. Meth.*, 53:221-33, 2003). However, as novel methods to easily and precisely measure an electrical or electrochemical signal are attempted, there are increased demands for CNT as a new material.

The methods comprising preparing a high density CNT multiplayer, attaching DNA thereon and detecting complementary DNA are useful in genotyping, mutation detection, pathogen identification and the like. It has been reported that PNA (peptide nucleic acid: DNA mimic) is regio-specifically fixed on a single walled CNT and the complementary binding to probe DNA is detected (Williams, K. A. et al., *Nature*, 420:761, 2001). Also, there has been an example, in which an oligonucleotide was fixed on a CNT array by a electrochemical method and DNA was detected by guanine oxidation (Li, J. et al., *Nano Lett.*, 3:597-602, 2003). However, these methods do not apply CNT to fabrication and development of biochips.

Recently, a high capacity biomolecule detection sensor using CNT was disclosed (WO 03/016901 A1). This patent relates to a multi-channel type biochip produced by arranging a plurality of CNTs on a substrate using a chemical linker and attaching various types of receptors. However, it has a disadvantage of relative weakness to environmental changes.

Therefore, the present inventors have found a method for producing a CNT-biochip by repeated laminating CNT on a substrate having exposed amine groups by chemical bonding to form a high density CNT film or pattern having exposed chemical functional groups and chemically binding a bio-receptor to the CNT film or pattern, or treating the CNT surface with a chemical to prevent the non-specific binding by physical adsorption and chemically binding the bio-receptor to the treated surface, and completed the present invention.

SUMMARY OF THE INVENTION

It is an object of the present invention to provide a high density CNT film repeatedly immobilized on a substrate by chemical bonding and having chemical functional groups exposed on its surface, a CNT-biochip comprising bio-receptors attached onto the surface of the CNT film, and a method for preparing the same.

It is another object of the present invention to provide a CNT-biochip comprising a bio-receptor attached to a desired position on a high density CNT pattern laminated by chemical bond and a method for preparing the same.

It is a further object of the present invention to provide a method for detecting various target biomaterials capable of binding to or reacting with a bio-receptor using the CNT-biochip.

To achieve the above objects, the present invention provides a method for producing a high density CNT film or pattern having a carboxyl group, exposed on its surface, which comprises the steps of: (a) reacting a substrate having amine groups exposed on the surface or a substrate having amine groups exposed in a patterned substrate with CNT having exposed carboxyl groups to form a CNT single layer or single layer pattern on the surface of substrate by amidation reaction between the amine group and the carboxyl group; (b) reacting the CNT single layer or single layer pattern with a diamine type organic compounds to modify the CNT single layer with an organic amine group and reacting the organic amine with the CNT having exposed carboxyl groups to laminate a CNT layer thereon; and (c) repeating the step (b) n times to form CNT layers and organic amine groups laminated alternately for n times, thereby forming a high density CNT film or pattern having exposed carboxyl groups.

The present invention also provides a high density CNT film or pattern which is prepared by the above-described method and has a carboxyl group exposed on its surface.

The present invention also provides a CNT-biochip comprising a bio-receptor fixed to the carboxyl group exposed on the CNT film or pattern by chemical or physicochemical bond, in which the bio-receptors have a functional group capable of binding to the carboxyl group and a method for fabricating the same.

Also, the present invention provides a method for producing a high density CNT film or pattern having a chemical functional group selected from the group consisting of amine group, aldehyde group, hydroxyl group, thiol group and halogen, exposed on its surface, which comprises the steps of (a) reacting a substrate having amine groups exposed on the surface or a substrate having amine groups exposed in a pattern with CNT having exposed carboxyl groups to form a CNT single layer or single layer pattern on the surface of substrate by amidation reaction between the amine group and the carboxyl group; (b) reacting the CNT single layer or single layer pattern with a diamine type organic compound to form an organic amine layer on the CNT single layer and reacting the organic amine with the CNT having exposed carboxyl groups to laminate a CNT layer thereon; (c) repeating the step (b) n times to form CNT layers and organic amine layers laminated alternately for n times, thereby forming a high density CNT film or pattern having exposed carboxyl groups; and (d) modifying the high density CNT film or pattern having exposed carboxyl groups with a chemical compound having both a functional group capable of binding to the carboxyl group and a chemical functional group selected from the group consisting of amine group, aldehyde group, hydroxyl group, thiol group and halogen.

The present invention also provides a high density CNT film or pattern which is prepared by the above-described method and has a chemical functional group exposed on its surface, in which the chemical functional group is selected from the group consisting of amine group, aldehyde group, hydroxyl group, thiol group and halogen.

The present invention also provides a CNT-biochip comprising a bio-receptor fixed to a chemical functional group, selected from the group consisting of amine group, aldehyde group, hydroxyl group, thiol group and halogen, exposed on the CNT film or pattern by chemical or physicochemical bond, in which the bio-receptor has a functional group capable of binding to the chemical functional group, and a method for fabricating the same.

According to the present invention, the substrate having amino functional groups exposed on its surface can be prepared by treating a substrate with aminoalkyloxysilane, the substrate having the amine groups exposed in a pattern can be prepared by forming a photoresist or organic supra-molecule pattern on a substrate having the exposed amine groups. CNT can be laminated or fixed on such pattern in the vertical or horizontal direction. In the case of a nanopattern of an organic supra-molecule, CNT is preferably fixed in the vertical direction. The substrate having the amine groups exposed in a pattern is prepared by forming a photoresist pattern on a substrate having exposed amine groups using photolithography which is commonly used in the semiconductor process, or by forming a photoresist or organic supra-molecule pattern on a substrate, followed by treatment with aminoalkyloxysilane.

According to the present invention, the chemical functional group capable of binding to carboxyl group is preferably amine group or hydroxyl group. Also, the bio-receptor can be enzyme substrates, ligands, amino acids, peptides, proteins, DNA, RNA, PNA, lipids, cofactors or carbohydrates, which have carboxyl group, amine group, hydroxyl group, aldehyde group, or thiol group. The target biomaterial can be a substance able to serve as a target by reacting with or binding to the bio-receptor to be detected, including preferably proteins, nucleic acids, antibodies, enzymes, carbohydrates, lipids or other biomolecules derived from living bodies, more preferably DNA or proteins.

According to the present invention, the chemicals having both the functional group capable of binding to carboxyl group and the chemical functional group selected from the group consisting of amine group, aldehyde group, hydroxyl group, thiol group and halogen include $H_2N-R_1-NH_2$, $H_2N-R_2-CHO$, $H_2N-R_3-OH$, $H_2N-R_4-SH$, or $H_2N-R_5-X$ in which $R_1$, $R_2$, $R_3$, $R_4$ and $R_5$ are independently a $C_{1-20}$ saturated hydrocarbon, un-saturated hydrocarbon or aromatic organic group and X is halogen element.

Also, the present invention provides a method for detecting a target biomaterial capable of binding to or interacting with a bio-receptor, wherein the method is characterized by using the CNT-biochip according to the present invention.

Also, the present invention provides a CNT-DNA chip using DNA as a bio-receptor and a method for detecting DNA hybridization, wherein the method is characterized by using the CNT-DNA chip.

The term "CNT-biochip" used herein inclusively refers to composites having a bio-receptor chemically or physicochemically bonded to a CNT pattern and can be defined as biochips comprising a bio-receptor attached to a high density CNT pattern or film by chemical or physicochemical bond (particularly, amide bond).

According to the present invention, the CNT-biochip capable of detecting various types of target biomaterials directly or by an electrochemical or electric signal is fabricated by repeatedly laminating CNT on a solid substrate coated with a chemical functional group (amine group) by chemical bond to prepare a high surface density CNT pattern or film having exposed carboxyl groups and attaching a bio-receptor having a functional group (amine group, hydroxyl group, etc.) capable of chemically reacting with the carboxyl groups to the produced CNT pattern or film.

Meanwhile, in order to attach a bio-receptor without a functional group capable of binding to the carboxyl group, the CNT film or pattern having the exposed carboxyl group is modified with a chemical having both a chemical functional group (amine group, hydroxyl group, etc.) capable of binding to the carboxyl group and a chemical functional group capable of binding to the functional group of the target bio-receptor (amine group, hydroxyl group, thiol group, aldehyde group, etc.). Therefore, nearly all bio-receptors can be chemically or physicochemically attached to the high density CNT film or pattern.

For example, in order to attach a bio-receptor having thiol group, a CNT film or pattern is firstly modified with a chemical having both a chemical functional group capable of binding to the carboxyl group and the thiol functional group (Ex.: $NN_2-R_2-SH$) so that the thiol functional group is exposed on the surface of the CNT film or pattern. Then, a bio-receptor having a thiol group is attached to the CNT film or pattern by S—S bond formation.

According to the present invention, by overcoming the limit of the conventional technologies growing CNT using a catalyst fixed at a predetermined position, it is possible to form a pattern in a desired shape at a desired position. Also, the present invention has improved the defects involved in the conventional technologies by forming a pattern on a substrate using a polymer or an organic supra-molecule so as to utilize advantage of chemical methods at maximum.

According to the present invention, an electric power source can be connected through at least one conductive nanowire so that charge can be applied to each liquid phase comprising the target biomaterials placed on the CNT or CNT chip, in which the conductive nanowire can be formed as a single atom according to the conventional technology (Kouwenhoven, L., Science, 275:1896-97, 1997), by forming a predetermined pattern on a conductive metal and depositing a wire, through which an electric current can flow, by ion implantation or sputtering.

BRIEF DESCRIPTION OF THE DRAWINGS

FIG. 5 shows the result of the hybridization using a DNA chip comprising DNA fixed on a high density CNT pattern, in which (a) shows a fluorescent image of the substrate comprising CNT having exposed carboxyl groups fixed with high density, before binding of DNA, (b) shows the result of the fluorescence detection upon hybridization with complementary DNA, and (c) shows the result of the fluorescence detection upon hybridization with non-complementary DNA.

FIG. 6 shows the result of the hybridization using a DNA chip comprising DNA fixed on a high density CNT film, in which (a) shows a fluorescent image of the high density CNT film, before binding of DNA, and (b) shows the result of the fluorescence detection on the hybridized sample, in which (1) is hybridized with complementary DNA and (2) is hybridized with non-complementary DNA.

FIG. 7 shows the result of the hybridization using a DNA chip comprising DNA fixed on a high density CNT film modified with amine group, in which (a) shows the result of the fluorescence detection upon hybridization with complementary DNA, and (b) shows the result of the fluorescence detection upon hybridization with non-complementary DNA.

DETAILED DESCRIPTION OF THE PREFERRED EMBODIMENT

The present invention will hereinafter be described in further detail by examples. However, it is to be understood that these examples can be modified into other various forms, and the scope of the present invention is not intended to be limited to such examples. Such examples are given to more fully describe the present invention for a person skilled in the art.

Reference will now be made in detail to the preferred embodiment of the present invention, an example of which is illustrated in the accompanying drawings.

Example 1

Preparation of CNT Having Exposed Carboxyl Groups

The CNT, which can be used in the present invention, is not particularly limited and can be commercially available products or prepared by a conventional method. Pure CNT should be carboxylated at its surface and/or both ends to be used in the present invention.

The pristine CNT was refluxed in a nitric acid for 45 hours at 90° C. and centrifuged. The residue was washed in distilled water and filtered through a 0.2 μm filter. The purified CNT was cut in a sonicator containing an oxidizing acid (a mixture of nitric acid and sulfuric acid) for 16 hours. The cut CNT having exposed carboxyl groups was filtered through a 0.1 μm filter to obtain CNT with a predetermined size.

Example 2

Preparation of a Substrate Having Exposed Amine Group

In the present invention, the substrate having exposed amine group was prepared by modifying with aminealkyloxysilane on a substrate such as silicon, glass, melted silica, plastics, PDMS (polydimethylsiloxane). However, commercially available substrates, which had been surface-treated with amine, can also be used.

Example 3

Figure 1A:
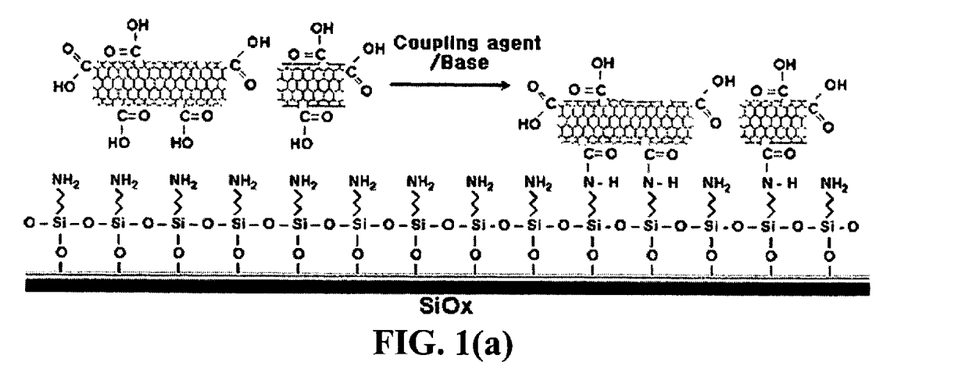
FIG. 1 is a schematic view of the process for preparing a high density CNT film by laminating CNT having exposed carboxyl groups by amidation reaction on a substrate having exposed amine groups.

Preparation of a High Density CNT Film Having Carboxyl Group Exposed on its Surface The CNT having exposed carboxyl groups, prepared in Example 1, was reacted with the substrate having exposed amine groups, prepared in Example 2 to form a CNT single layer on the substrate by amide bond formation between the carboxyl group and the amine group (FIG. 1(a)).

Figure 1B:
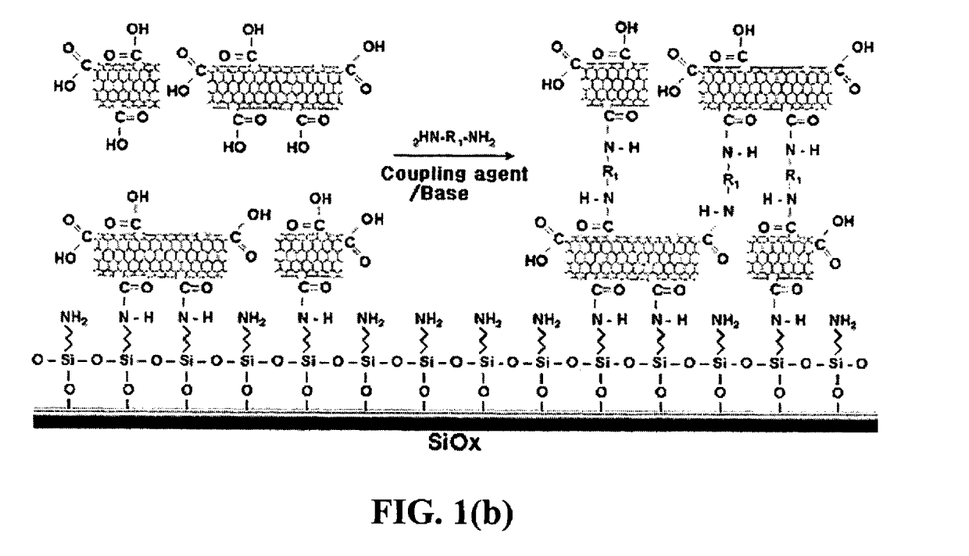

Then, the CNT attached to the substrate by amide bond was reacted with a diamine type organic compound having double amine functional groups while CNT having exposed carboxyl groups was reacted with amine groups at the other side of the diamine type organic compound to form another CNT layer by the formation of amide bond (FIG. 1(b)).

Figure 1C:
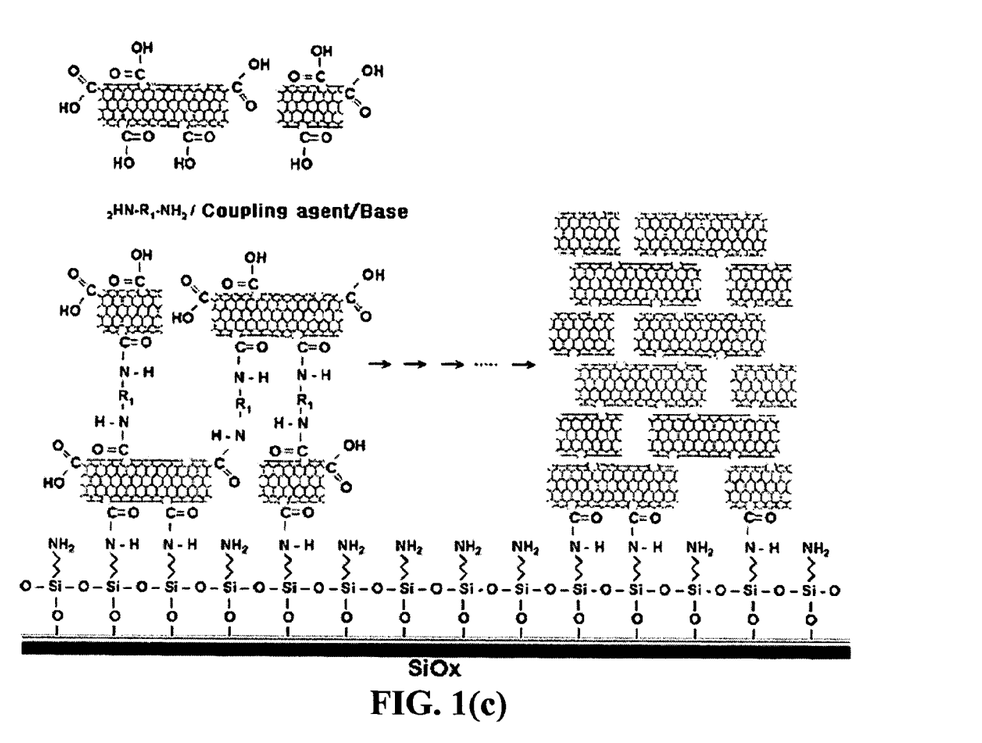

Next, the chemical reaction between the CNT having exposed carboxyl groups and the diamine type organic compound was repeated to prepare a high density CNT film comprising the CNT layer and the organic diamine layer laminated alternately for n times and having carboxyl groups exposed on its surface (FIG. 1(c)).

The diamine type organic compound which can be used in the present invention includes compounds having a formula of $HN_2$—$R_1$—$NH_2$, in which $R_1$ is $C_{1-20}$ saturated hydrocarbons, un-saturated hydrocarbons or aromatic organic group.

To accelerate the formation of the above amide bond, HAMDU(O-(7-azabenzotriazol-1-yl)-1,3-dimethyl-1,3-dimethyleneuronium hexafluorphosphate), DCC(1,3-dicyclohexyl carbodiimide), HAPyU(O-(7-azabenzotriazol-1-yl)-1,1:3,3-bis(tetramethylene)uronium hexafluorphosphate), HATU(O-(7-azabenzotriazol-1-yl)-1,1:3,3-tetra methyluronium hexafluorphosphate), HBMDU (O-(benzotriazol-1-yl)-1,3-dimethyl-1,3-dimethyleneuronium hexafluorphosphate), or HBTU(O-(benzotriazol-1-yl)-1,1,3,3-tetramethyluronium hexafluorophosphate) is preferably used as a coupling agent, and DIEA (diisopropylethylamine), TMP(2,4,6-trimethylpyridine), or NMI (N-methylimidazole) is preferably used as a base.

Also, in the case of using water as solvent, EDC (1-ethyl-3-(3-dimethylamini-propyl) arbodiimide hydrochloride) is preferably used as a coupling agent, and NHS(N-hydroxysuccinimide) or NHSS(N-hydroxysulfosuccinimide) is preferably used as a co-coupling agent (base).

In this Example, HATU was used as a coupling agent and DIEA was used as a base. The coupling agent participates in the formation of the amide bond (—CONH—) between the —COOH functional group and the —$NH_2$ functional group, and the base agent acts to increase the efficiency when the coupling agent forms the amide bond.

Example 4

A Substrate Having Amine Groups Exposed in a Pattern and Formation of a High Density CNT Pattern Using the Same In order to expose amine groups in a pattern on a substrate, 2 types of methods can be used. The first method includes forming a photoresist or organic supra-molecular pattern on a substrate such as silicon, glass, melted silica, plastics, PDMS (polydimethylsiloxane) and fixing aminoalkyloxysilane on the substrate surface using the formed pattern as a mask to expose amine groups in a pattern on the substrate surface. The second method includes treating a substrate surface with aminoalkyloxysilane and forming a photoresist or organic supra-molecular pattern to expose amine groups in a pattern on the substrate surface. A preferred example of aminoalkyloxysilane is aminopropyltriethoxysilane.

Using the substrate having amine groups exposed in a pattern, the process described in Example 3 was repeated to form a high density CNT pattern having carboxyl groups exposed on its surface.

The CNT pattern having exposed carboxyl groups can be modified by chemicals having both a chemical functional group (amine group, hydroxyl group, etc.) capable of reacting with the carboxyl group and a chemical functional group (amine group, hydroxyl group, thiol group, aldehyde group, etc.) capable of binding to a functional group of a desired bio-receptor. The chemicals which can be used in such modification include $H_2N$—$R_1$—$NH_2$, $H_2N$—$R_2$—CHO, $H_2N$—$R_3$—OH, $H_2N$—$R_4$—SH, $H_2N$—$R_5$—X and the like, in which $R_1$, $R_2$, $R_3$, $R_4$ and $R_5$ are independently a $C_{1-20}$ saturated hydrocarbon, un-saturated hydrocarbon or aromatic organic group and X is halogen element.

Example 5

Fabrication of a DNA Chip Comprising DNA Fixed on a CNT Film

Figure 2:
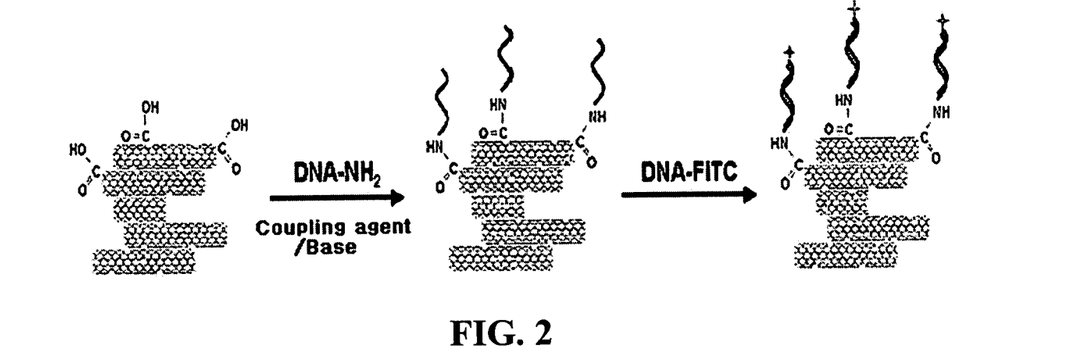
FIG. 2 shows the process for hybridization of complementary DNA to a CNT-DNA chip prepared by attaching DNA having amine groups to a CNT pattern or film having exposed carboxyl groups.

A CNT-DNA chip was fabricated by attaching a mine groups of DNA to the CNT film having exposed carboxyl groups, prepared in Example 3 (FIG. 2). In this Example, EDC was used as a coupling agent for the formation of the amide bond between the carboxyl group and the amine group and NHS was used as a base agent. Also, in this Example, a CNT-DNA chip was fabricated using oligonucleotide having the following SEQ ID NO: 1 having amine group as the terminal group.

SEQ ID NO 1: 5'-TGT GCC ACC TAC AAG CTG TG-3'

Figure 4:
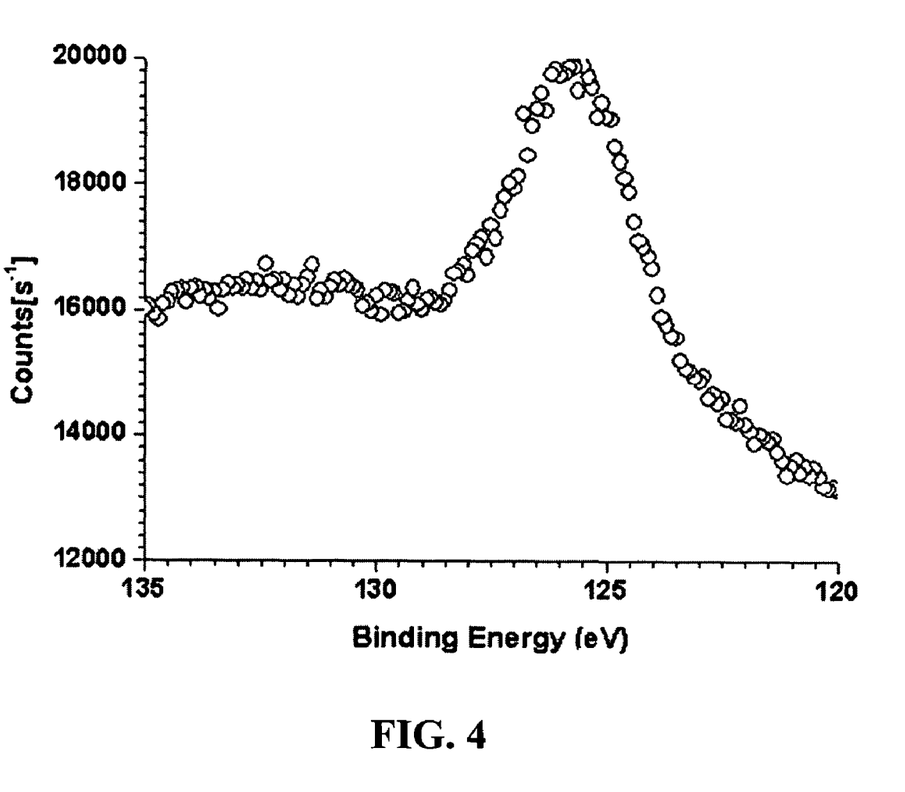
FIG. 4 is an XPS spectrum for phosphorous detected on the surface of the CNT pattern or film having DNA chemically bonded.

The existence of DNA on the CNT film was confirmed by XPS (X-ray photoelectron spectroscope) spectrum for phosphorus atom considering the fact that all DNAs have phosphate groups (FIG. 4). As shown in FIG. 4, phosphorus was detected in the XPS surface analysis and thus, it was confirmed that DNA was attached to the CNT surface.

Figure 3:
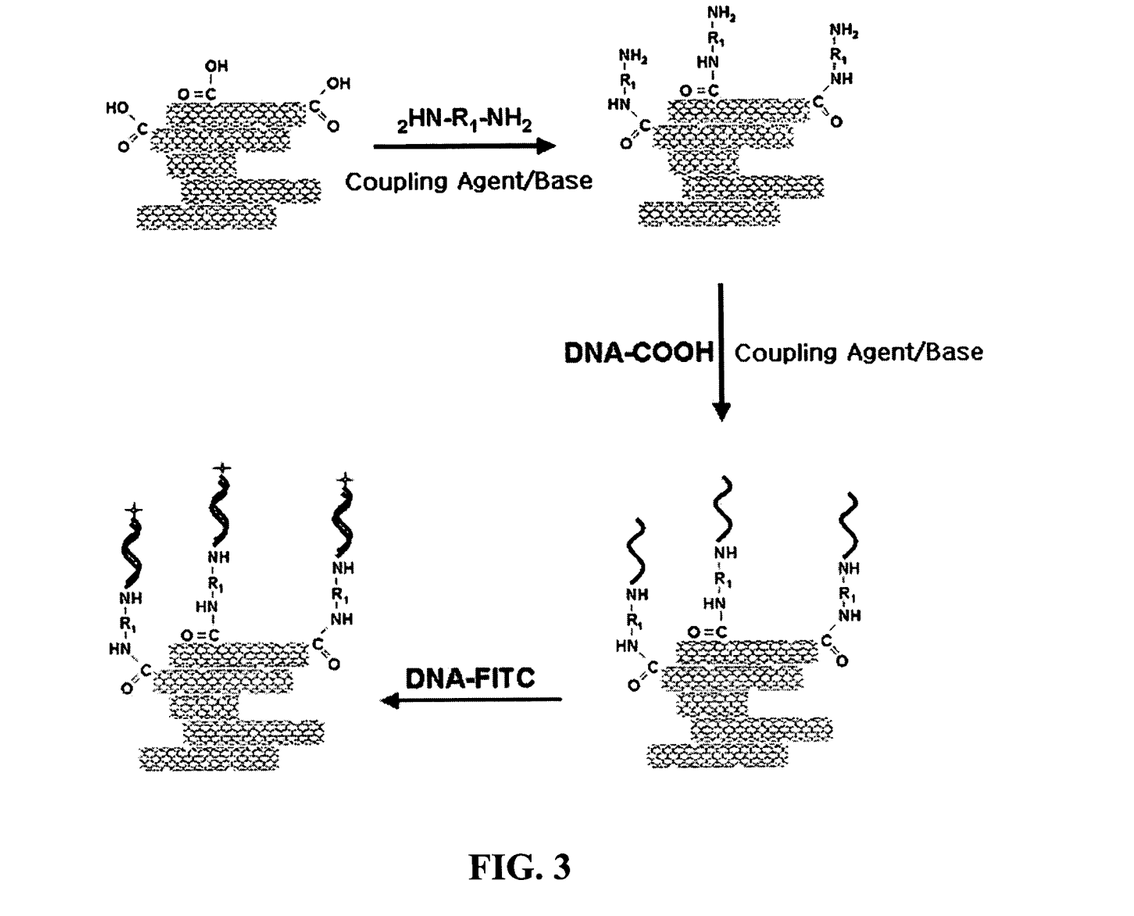
FIG. 3 shows the process for hybridization of complementary DNA to a CNT-DNA chip prepared by modifying a CNT pattern or film having exposed carboxyl groups with amine groups and attaching DNA having carboxyl group as the terminal group thereto.

In this Example, a CNT-DNA chip was fabricated by attaching carboxyl groups of DNA to the CNT film having amine groups exposed on the surface, prepared in Example 3 (FIG. 3). In this Example, EDC was used as a coupling agent for the formation of the amide bond between the carboxyl group and the amine group and NHS was used as a co-coupling agent. Also, in this Example, a CNT-DNA chip was fabricated using oligonucleotide having the SEQ ID NO 1 having carboxyl group as the terminal group.

Example 6

Fabrication of a DNA Chip Comprising DNA Fixed on a CNT Pattern

In this example, a DNA chip was fabricated by attaching amine group of DNA to the CNT pattern having exposed carboxyl groups, prepared in Example 4 (FIG. 2). Alternatively, a DNA chip can be fabricated by modifying the CNT pattern having exposed carboxyl groups, prepared in Example 4, with a diamine type organic compound having amino functional groups at both sides to expose amino functional groups and attaching carboxyl groups of DNA to the amine groups (FIG. 3).

Example 7

Analysis of Hybridization Using a CNT-DNA Chip

The DNA chip prepared in Example 6 was placed in a hybridization chamber and a hybridization solution was dropped at where the CNT had been fixed. Then, a cover slide was placed thereon. Here, the hybridization solution was prepared with 32 µl of a solution containing an oligonucleotide of complementary sequence to be a total volume of 40 µg at a final concentration 3XSSC (0.45M NaCl, 0.045M sodium citrate) and 0.3% SDS (sodium dodecyl sulfate). The complementary oligonucleotide sequence was the following SEQ ID NO 2 having FITC (fluorescein isothiocyanate) attached to its end.

SEQ ID NO 2: 5'-CAC AGC TTG TAG GTG GCA CA-3'

The solution was left at 100° C. for 2 minutes and centrifuged for 2 minutes at 12000 rpm to remove non-specific binding between two oligonucleotide strands. In order to prevent the hybridization solution from being dried in the hybridization chamber, 30 µl of 3XSSC (0.45M NaCl, 0.045M sodium citrate) was placed in each hollow at both sides of the chamber and the chamber was closed and hybridized for 10 hours at 55° C. in a incubator.

Figure 5A:
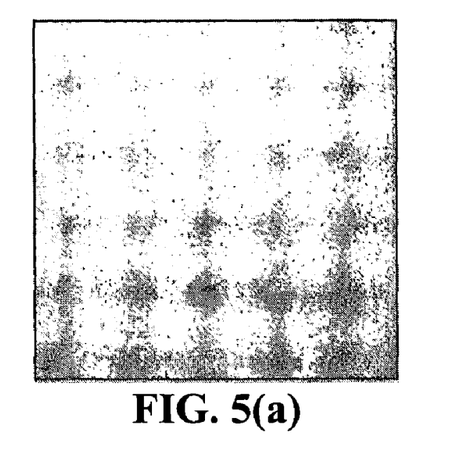
Figure 5B:
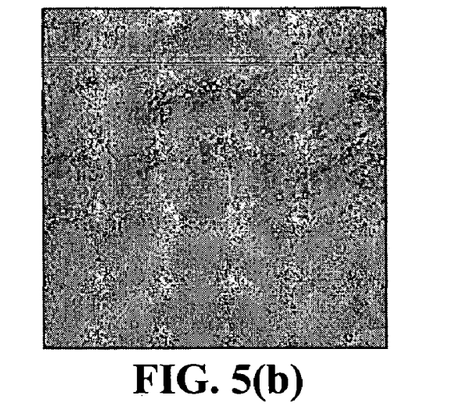
Figure 5C:
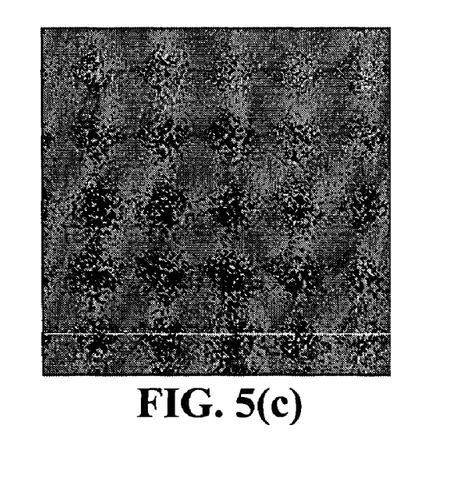

The hybridization was detected through a fluorescent image using FITC labeled at the end of the oligonucleotide of the SEQ ID NO 2. The fluorescent image was obtained using ScanArray 5000 (Packard BioScience, BioChip Tecnologies LLC) confocal microscope and the QuantArray Microarray Analysis Software (FIG. 5). In FIG. 5, (a) shows a fluorescent image of the substrate comprising CNT having exposed carboxyl groups fixed thereon with high density, before binding of DNA, (b) shows the result of the fluorescence detection upon hybridization with complementary DNA, and (c) shows the result of the fluorescence detection upon hybridization with non-complementary DNA. It was confirmed that the fluorescence was clear and even when the oligonucleotide having the sequence complementary to the CNT-DNA chip was hybridized (FIG. 5(b)). However, in the CNT pattern without the oligonucleotide fixed thereon (FIG. 5(a)) and in the CNT-DNA chip hybridized with the oligonucleotide having the non-complementary sequence (FIG. 5(c)), no fluorescence was observed. From these results, it was confirmed that the non-specific reaction almost never occurred.

Figure 6A:
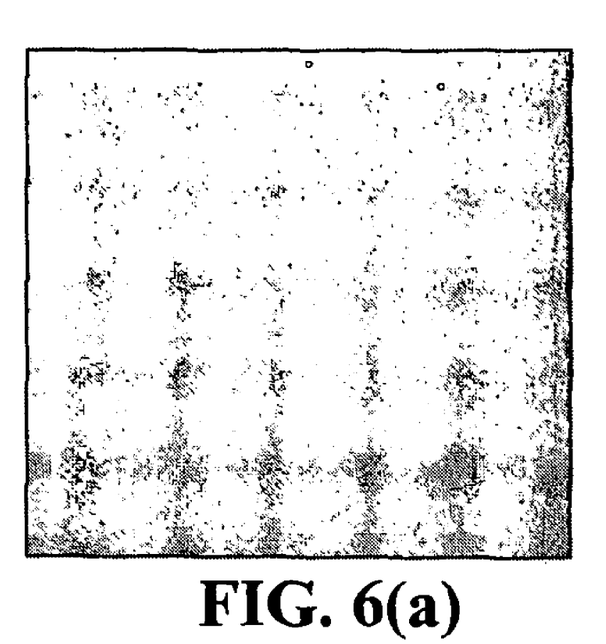
Figure 6B:
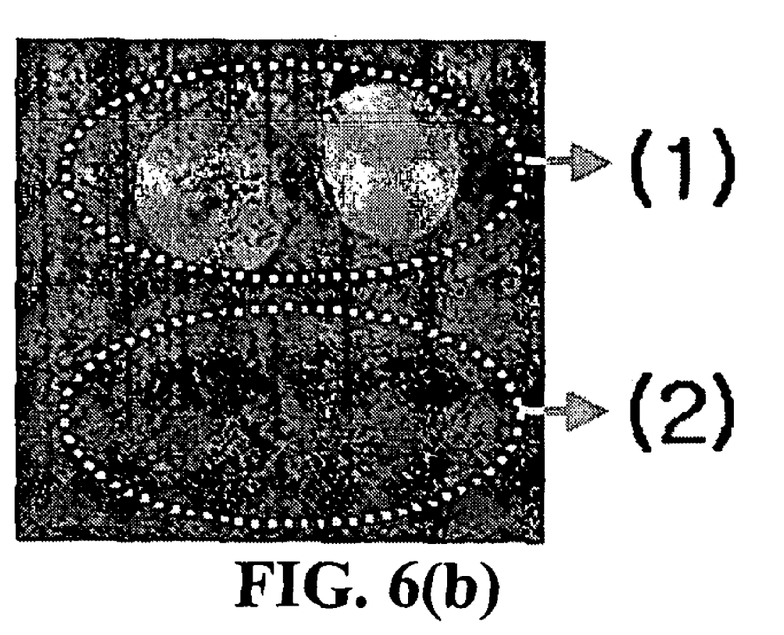

Also, a hybridization was performed following the process as described above using the CNT-DNA chip prepared in Example 5 (FIG. 6). FIG. 6(a) shows a fluorescent image of the high density CNT film, before binding of DNA, and FIG. 6(b)(1) is the result of the fluorescence detection upon hybridization with complementary DNA and (2) is the result of the fluorescence detection upon hybridization with non-complementary DNA. When the oligonucleotide having the sequence complementary to the oligonucleotide bonded to the CNT film was hybridized, the fluorescence was clear and even ((1) of FIG. 6(b)). However, in the CNT film without fixed oligonucleotide (FIG. 6(a)) and in the CNT-film hybridized with the oligonucleotide having the sequence non-complementary to the oligonucleotide bonded to the CNT film ((2) of FIG. 6(b)), no fluorescence was observed. From these results, it was confirmed that the non-specific reaction almost never occurred.

Figure 7:
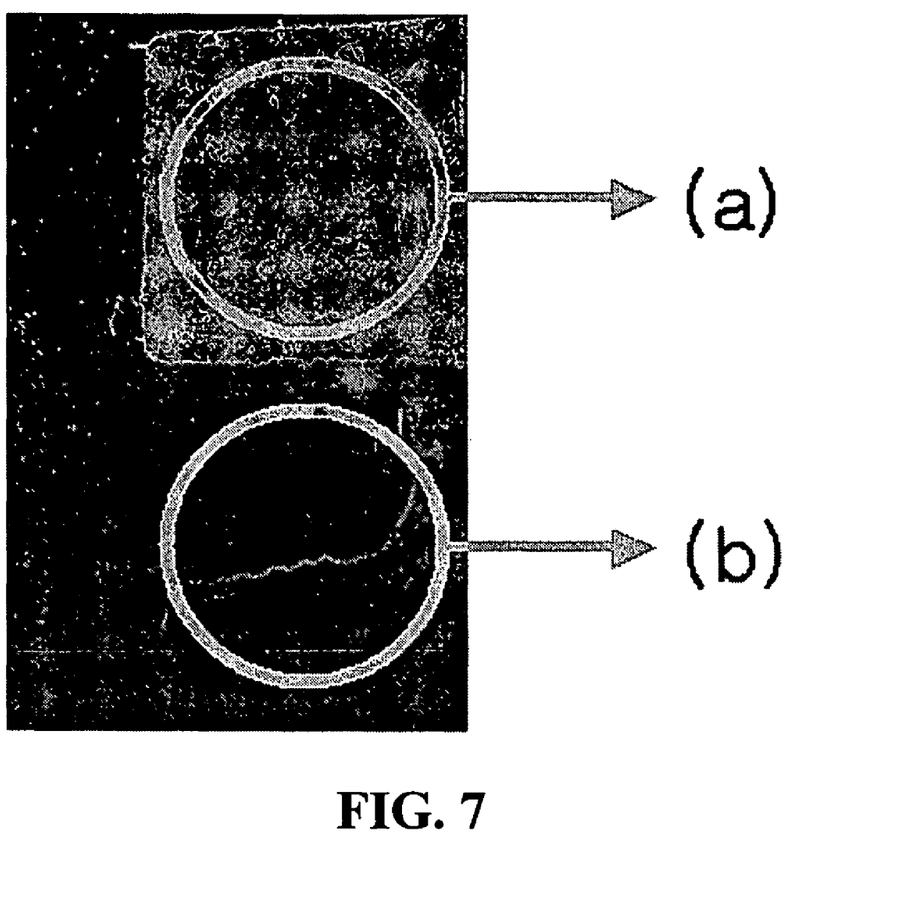

In this Example, a hybridization was performed following the process as described above using the CNT-DNA chip prepared in Example 5 (FIG. 7). In FIG. 7, (a) shows the result of the fluorescence detection upon hybridization with complementary DNA and (b) shows the result of the fluorescence detection upon hybridization with non-complementary DNA. As shown in FIG. 7, it was possible to certainly distinguish between the hybridized sample and the non-hybridized sample.

As described above, the present invention provides a high density CNT film produced by repeatedly fixing CNT having carboxyl groups exposed on a substrate having exposed amine groups by amidation reaction and a biochip comprising a bio-receptor attached chemically or physicochemically to a chemical functional group on the surface of the CNT film. Also, the present invention provides a biochip comprising a bio-receptor bonded chemically with a high density CNT pattern produced by laminating CNT having exposed carboxyl groups at a desired position on a substrate.

According to the present invention, it is possible to fabricate various types of CNT-biochips by chemically or physicochemically attaching various bio-receptors to a CNT pattern (or film) having exposed carboxyl groups or a CNT pattern (or film) having the exposed functional groups modified by various chemical groups. Also, it is possible to fabricate a CNT-biochip comprising bio-receptors attached evenly with a high density on a surface of a CNT film where chemical functional groups are abundant and present evenly. Further, the chemical functional groups on the CNT surface can be modified into various functional groups by chemical manipulation.

Particularly, upon fluorescent measurement of DNA hybridization using the CNT-DNA chip according to the present invention, it is possible to reduce unnecessary signals, thereby producing excellent results. The CNT-DNA chip is useful for genotyping, mutation detection, pathogen identification and the like.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A method for producing a high density CNT film or pattern consisting of laminated CNT layers, wherein the layers are bound together by reaction of a carboxyl group and an amine group and wherein a top layer has exposed carboxyl groups on the surface thereof, and wherein the method for producing the CNT film or pattern comprises the steps of:

(a) reacting a substrate having amine groups exposed on the surface or a substrate having amine groups exposed in a pattern with CNT having exposed carboxyl groups to form a CNT single layer or single layer pattern on the surface of the substrate by amidation reaction between the amine groups and the carboxyl groups;

(b) reacting the CNT single layer or single layer pattern with an organic diamine to modify the CNT single layer with organic amine groups and reacting the organic amine groups with the CNT having exposed carboxyl groups to laminate a CNT layer thereon, wherein the CNT layer is laminated directly on the CNT single layer or single layer pattern by reaction of the amine groups and the carboxyl groups; and (c) repeating the step (b) to form laminated CNT layers, thereby forming a high density CNT film or pattern having exposed carboxyl groups.

2. The method according to claim 1, wherein the substrate is selected from the group consisting of silicon, glass, melted silica, plastics and PDMS.

3. The method according to claim 1, wherein the substrate having amine groups exposed on its surface is prepared by treating the substrate with aminoalkyloxysilane.

4. The method according to claim 1, wherein the substrate having the amine groups exposed in a pattern is prepared by forming a photoresist or organic supra-molecule pattern on the substrate having the exposed amine groups.

5. The method according to claim 1, wherein the substrate having the amine groups exposed in a pattern is prepared by forming a photoresist or organic supra-molecule pattern on a substrate, followed by treatment with aminoalkyloxysilane.

6. A high density carbon nanotube (CNT) film or pattern consisting of laminated CNT layers, wherein the layers are bound together by reaction of a carboxyl group and an amine group and wherein a top layer has exposed carboxyl groups on the surface thereof, and wherein the CNT film or pattern is prepared by a method comprising the steps of:

(a) reacting a substrate having amine groups exposed on the surface or a substrate having amine groups exposed in a pattern with CNT having exposed carboxyl groups to form a CNT single layer or single layer pattern on the surface of the substrate by amidation reaction between the amine groups and the carboxyl groups;

(b) reacting the CNT single layer or single layer pattern with an organic diamine to modify the CNT single layer with organic amine groups and reacting the organic amine groups with the CNT having exposed carboxyl groups to laminate a CNT layer thereon, wherein the CNT layer is laminated directly on the CNT single layer or single layer pattern by reaction of the amine groups and the carboxyl groups; and (c) repeating step (b) to form laminated CNT layers, thereby forming a high density CNT film or pattern having exposed carboxyl groups.

7. A method for fabricating a CNT-biochip comprising bio-receptors fixed to carboxyl groups exposed on the CNT film or pattern according to claim 6 by chemical or physicochemical bond, in which each bio-receptor has a functional group capable of binding to a carboxyl group.

8. The method according to claim 7, wherein the chemical functional group capable of binding to a carboxyl group is an amine group or a hydroxyl group.

9. A CNT-biochip which is prepared by the method according to claim 7, and comprising bio-receptors fixed to carboxyl groups exposed on the CNT film or pattern by chemical or physicochemical bond, in which each bio-receptor has a functional group capable of binding to a carboxyl group.

10. The CNT-biochip according to claim 9, wherein the bio-receptor is selected from the group consisting of a enzyme substrate, a ligand, an amino acid, a peptide, protein, DNA, RNA, PNA, lipid, a cofactor and a carbohydrate.

11. The CNT-biochip according to claim 10, wherein the bio-receptor is DNA.

12. A method for detecting a target biomaterial capable of binding to or interacting with a bio-receptor, wherein the method is characterized by using the CNT-biochip according to claim 9.

13. A method for detecting DNA hybridization, wherein the method is characterized by using the CNT-DNA chip according to claim 11.

14. A method for producing a high density CNT film or pattern consisting of laminated CNT layers wherein the layers are bound together by reaction of a carboxyl group and an amine group and wherein a top layer has exposed chemical functional groups selected from the group consisting of amine groups, aldehyde groups, hydroxyl groups, thiol groups and halogens, on its surface, and wherein the CNT film or pattern is prepared by a method comprising the steps of:

(a) reacting a substrate having amine groups exposed on the surface or a substrate having amine groups exposed in a pattern with CNT having exposed carboxyl groups to form a CNT single layer or single layer pattern on the surface of the substrate by amidation reaction between the amine groups and the carboxyl groups;

(b) reacting the CNT single layer or single layer pattern with an organic diamine to form an organic amine layer on the CNT single layer and reacting the organic amine groups with the CNT having exposed carboxyl groups to laminate a CNT layer thereon, wherein the CNT layer is laminated directly on the CNT single layer or single layer pattern by reaction of the amine groups and the carboxyl groups;

(c) repeating the step (b) to form laminated CNT layers, thereby forming a high density CNT film or pattern having exposed carboxyl groups; and (d) modifying the high density CNT film or pattern having exposed carboxyl groups with a chemical compound having both a functional group capable of binding to a carboxyl group and a chemical functional group selected from the group consisting of amine group, aldehyde group, hydroxyl group, thiol group and halogen.

15. The method according to claim 14, wherein the substrate is selected from the group consisting of silicon, glass, melted silica, plastics and PDMS.

16. The method according to claim 14, wherein the substrate having amine groups exposed on its surface is prepared by treating the substrate with aminoalkyloxysilane.

17. The method according to claim 14, wherein the substrate having the amine groups exposed in a pattern is prepared by forming a photoresist or organic supra-molecule pattern on the substrate having the exposed amine groups.

18. The method according to claim 14, wherein the substrate having the amine groups exposed in a pattern is prepared by forming a photoresist or organic supra-molecule pattern on a substrate, followed by treatment with aminoalkyloxysilane.

19. The method according to claim 14, wherein the chemical functional group capable of binding to a carboxyl group is an amine group or a hydroxyl group.

20. The method according to claim 14, wherein the chemical compound having both a functional group capable of binding to a carboxyl group and a chemical functional group selected from the group consisting of amine group, aldehyde group, hydroxyl group, thiol group and halogen include $H_2N-R_1-NH_2$, $H_2N-R_2-CHO$, $H_2N-R_3-OH$, $H_2N-R_4-SH$, or $H_2N-R_5-X$ in which $R_1$, $R_2$, $R_3$, $R_4$ and $R_5$ are independently a $C_{1-20}$ saturated hydrocarbon, un-saturated hydrocarbon or aromatic organic group and X is halogen element.

21. A high density CNT film or pattern consisting of laminated CNT layers wherein the layers are bound together by reaction of a carboxyl group and an amine group and wherein a top layer has exposed carboxyl groups on the surface thereof, and wherein the CNT film or pattern is prepared by a method comprising the steps of:

(a) reacting a substrate having amine groups exposed on the surface or a substrate having amine groups exposed in a pattern with CNT having exposed carboxyl groups to form a CNT single layer or single layer pattern on the surface of the substrate by amidation reaction between the amine groups and the carboxyl groups;

(b) reacting the CNT single layer or single layer pattern with an organic diamine to form an organic amine layer on the CNT single layer and reacting the organic amine groups with the CNT having exposed carboxyl groups to laminate a CNT layer thereon, wherein the CNT layer is laminated directly on the CNT single layer or single layer pattern by reaction of the amine groups and the carboxyl groups;

(c) repeating step (b) to form laminated CNT layers, thereby forming a high density CNT film or pattern having exposed carboxyl groups; and (d) modifying the high density CNT film or pattern having exposed carboxyl groups with a chemical compound having both a functional group capable of binding to a carboxyl group and a chemical functional group selected from the group consisting of amine group, aldehyde group, hydroxyl group, thiol group and halogen;

wherein the high density CNT film or pattern has exposed chemical functional groups on its surface, in which the chemical functional groups are any one selected from the group consisting of amine groups, aldehyde groups, hydroxyl groups, thiol groups and halogens.

22. A method for fabricating a CNT-biochip comprising bio-receptors fixed to the chemical functional groups according to claim 21 by chemical or physicochemical bond, in which the bio-receptors each have a functional group capable of binding to a chemical functional group.

23. A method according to claim 22, wherein the chemical compound having both a functional group capable of binding to a carboxyl group and a chemical functional group selected from the group consisting of amine group, aldehyde group, hydroxyl group, thiol group and halogen include $H_2N-R_1-NH_2$, $H_2N-R_2-CHO$, $H_2N-R_3-OH$, $H_2N-R_4-SH$, or $H_2N-R_5-X$ in which $R_1$, $R_2$, $R_3$, $R_4$ and $R_5$ are independently a $C_{1-20}$ saturated hydrocarbon, un-saturated hydrocarbon or aromatic organic group and X is halogen element.

24. A CNT-biochip which is prepared by the method according to claim 22.

25. The CNT-biochip according to claim 24, wherein the bio-receptor is selected from the group consisting of a enzyme substrate, a ligand, an amino acid, a peptide, protein, DNA, RNA, PNA, lipid, a cofactor and a carbohydrate.

26. The CNT-biochip according to claim 25, wherein the bio-receptor is DNA.

27. A method for detecting a target biomaterial capable of binding to or interacting with a bio-receptor, wherein the method is characterized by using the CNT-biochip according to claim 24.

28. A method for detecting DNA hybridization, wherein the method is characterized by using the CNT-DNA chip according to claim 26.

* * * * *

UNITED STATES PATENT AND TRADEMARK OFFICE
CERTIFICATE OF CORRECTION

PATENT NO. : 8,067,341 B2
APPLICATION NO. : 10/805044
DATED : November 29, 2011
INVENTOR(S) : Hee Tae Jung It is certified that error appears in the above-identified patent and that said Letters Patent is hereby corrected as shown below:

Cover page, "References Cited" "Other Publications" Col. 2, 2nd Reference author name "Cal, H" should be -- Cai, H --.

Cover page, "References Cited" "Other Publications" Col. 2, 3rd Reference author name "Cal, H" should be -- Cai, H --.

Column 2, line 56: "patent" should be -- application --.

Column 4, line 53: "X is halogen element" should be -- X is a halogen element --.

Column 5, line 27: "$NN_2$-$R_2$-SH" should be -- $H_2N$-$R_4$-SH --.

Column 7, line 25: "$HN_2$-$R_1$-$NH_2$" should be -- $H_2N$-$R_1$-$NH_2$ --.

Column 8, line 18: "X is halogen element" should be -- X is a halogen element --.

Column 8, line 26: "a mine" should be -- amine --.

Column 13, line 46-47: "X is halogen element" should be -- X is a halogen element --.

Column 14, line 39: "X is halogen element" should be -- X is a halogen element --.

Signed and Sealed this
Twenty-ninth Day of May, 2012

David J. Kappos
*Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 1
tgtgccacct acaagctgtg                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
cacagcttgt aggtggcaca                                                    20
```